United States Patent [19]

Jolles

[11] 4,284,625

[45] Aug. 18, 1981

[54] NAPHTHACENE PHARMACEUTICAL COMPOSITIONS AND METHOD OF USE

[75] Inventor: Georges Jolles, Sceaux, France

[73] Assignee: Rhone-Poulenc S.A., Paris, France

[21] Appl. No.: 652,848

[22] Filed: Jan. 27, 1976

Related U.S. Application Data

[60] Division of Ser. No. 307,955, Nov. 20, 1972, Pat. No. 3,965,088, which is a continuation-in-part of Ser. No. 187,559, Oct. 7, 1971, Pat. No. 3,957,755, which is a continuation-in-part of Ser. No. 768,532, Oct. 17, 1968, abandoned.

[30] Foreign Application Priority Data

Oct. 18, 1967 [FR] France .................. 67.124943

[51] Int. Cl.³ .............. A61K 31/71; C07H 15/22
[52] U.S. Cl. .................. 424/180; 536/17 A; 536/4
[58] Field of Search .................. 424/180, 181; 260/210 AB, 210 R; 536/17, 4, 17 A

[56] References Cited

U.S. PATENT DOCUMENTS 3,590,028  6/1971  Arcamone et al. .......... 260/210 AB
3,686,163  8/1972  Arcamone et al. .......... 260/210 AB

*Primary Examiner*—Johnnie R. Brown
*Attorney, Agent, or Firm*—Stevens, Davis, Miller & Mosher

[57] ABSTRACT

Naphthacene derivatives of the formula:

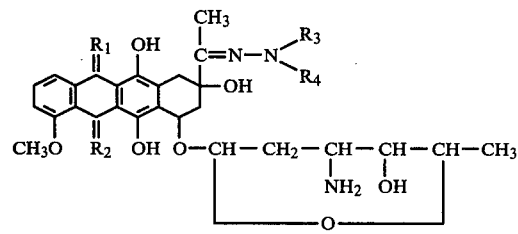

wherein each of $R_1$ and $R_2$ represents an oxygen atom or a group of the formula

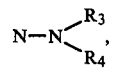

and $R_3$ represents hydrogen, or an alkyl, alkanoyl, thioalkanoyl, aryl, aroyl, carbamoyl, thiocarbamoyl, methylthiocarbamoyl or amidino group, these groups being optionally substituted, and $R_4$ represents hydrogen, or $R_3$ and $R_4$ together with the nitrogen atom to which they are attached represent piperazin-1-yl which carries on the second nitrogen atom an optionally substituted alkyl group, particularly 4-methoxy-5,12-dioxo-6,9,11-trihydroxy-7-(2,3,6-0-tridesoxy-3-amino-1-L-lyxohexosyl)-9-(1-formylhydrazono-ethyl)-5,7,8,9,10,12-hexahydro-naphthacene, and non-toxic salts thereof, posses anti-tumour properties.

20 Claims, No Drawings

NAPHTHACENE PHARMACEUTICAL COMPOSITIONS AND METHOD OF USE

This is a division of application Ser. No. 307,955 filed Nov. 20, 1972, now U.S. Pat. No. 3,965,088, which in turn is a continuation-in-part of appln. Ser. No. 187,559 filed Oct. 7, 1971, now U.S. Pat. No. 3,957,755, itself a continuation-in-part of appln. Ser. No. 768,532 filed Oct. 17, 1968 (now abandoned).

This invention relates to new therapeutically useful naphthacene derivatives, to a process for their preparation and pharmaceutical compositions containing them.

According to the present invention, there are provided the new naphthacene derivatives of the general formula:

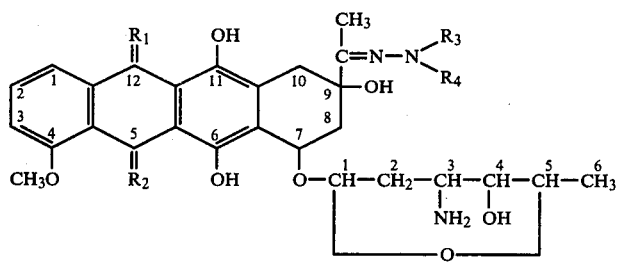

wherein $R_1$ and $R_2$ are the same or different and each represents an oxygen atom or a group of the formula

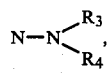

and $R_3$ represents a hydrogen atom or an alkyl, alkanoyl, thioalkanoyl, aryl (e.g. phenyl), aroyl (e.g. benzoyl), carbamoyl, thiocarbamoyl, methylthiocarbamoyl or amidino group, these groups being optionally substituted, and $R_4$ represents a hydrogen atom, or $R_3$ and $R_4$ together with the nitrogen atom to which they are attached represent a piperazin-1-yl group which carries on the second nitrogen atom an optionally substituted alkyl group, and salts thereof. The substituents which may be present on the groups $R_3$ and on the alkyl group in the 4-position of the piperazinyl ring when

represents a 4-alkylpiperazin-1-yl group are preferably substituents of acid or basic character which are able to improve the solubility of the naphthacene derivatives of formula I in water. Preferably the substituents are quaternary ammonium and sulphonic acid groups, or residues of amino acids and of peptides. The alkyl, alkanoyl and thioalkanoyl groups mentioned above preferably contain at most 4 carbon atoms.

According to a feature of the present invention, the naphthacene derivatives of general formula I are prepared by reacting a compound of the general formula:

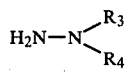

with the naphthacene derivative of the formula:

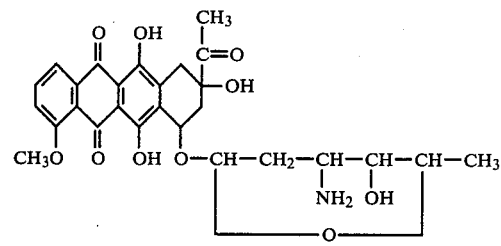

or acid addition salt thereof. The reaction is carried out under the usual conditions for the conversion of ketones to hydrazone compounds, and is preferably effected in an inert organic solvent such as an alcohol (e.g. ethanol) or dimethylformamide, with gentle heating.

When it is desired to obtain a naphthacene product of formula I wherein $R_1$ or $R_2$ represents a group

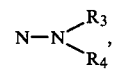

or $R_1$ and $R_2$ both represent groups

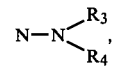

two moles or three moles of the starting material of formula II are required, respectively, for each mole of the naphthacene compound of formula III.

The naphthacene derivative of formula III is the antibiotic designated by the number 13,057 R.P., which has been given the name "daunorbicin". Its preparation and physico-chemical properties have been described in British Pat. No. 985,598 granted to Rhone-Poulenc S. A. on an application filed May 16th, 1963. In earlier publications it has been called "rubidomycin".

The naphthacene derivatives prepared by the aforementioned process may, where appropriate, be converted into acid addition salts or salts with nitrogen-containing bases, into metal salts or into quaternary ammonium salts. The salts may be obtained by the reaction of the naphthacene derivatives of formula I with acids or bases in appropriate solvents. As organic solvents there may be used, for example, alcohols, ethers, ketones or chlorinated hydrocarbons. The salt which is formed is precipitated, if necessary after concentration of its solution, and is separated by filtration or decantation. The quaternary ammonium salts may be obtained by the reaction of esters on the naphthacene bases, optionally in an organic solvent, at room temperature or more rapidly with gentle heating.

The naphthacene derivatives of general formula I and their salts have interesting anti-tumour properties, combined with a low toxicity. They have proved particularly active (administered intraperitoneally) against leukaemia L1210 in mice. The experiments were carried out on one month old mice weighing 18 to 20 grams intraperitoneally grafted with $10^3$ leukaemia L1210 cells and treated with doses of the naphthacene derivative between 0.5 and 5 mg/kg. (i.p.). Preferred compounds of formula I are those wherein the symbol $R_3$ represents an alkanoyl group optionally carrying a sulphonic acid or quaternary ammonium (e.g. $(CH_3)_3N^+Cl^-$) group, or a thiocarbamoyl, methylthiocarbamoyl or amidino group, and salts thereof. Of outstanding importance are 4-methoxy-5,12-dioxo-6,9,11-trihydroxy-7-(2,3,6-O-tridesoxy-3-amino-1-L-lyxohexosyl)-9-[1-(thiosemicarbazono)ethyl]-5,7,8,9,10,12-hexahydronaphthacene, 4-methoxy-5- (or 12-) oxo-6,9,11-trihydroxy-7-(2,3,6-O-tridesoxy-3-amino-1-L-lyxohexosyl)-9-[1-(thiosemicarbazono)ethyl]-12- (or 5-) (thiosemicarbazono)-5,7,8,9,10,12-hexahydro-naphthacene, 4-methoxy-5,12-dioxo-6,9,11-trihydroxy-7-(2,3,6-O-tridesoxy-3-amino-1-L-lyxohexosyl)-9-[1-(4-methylthiosemicarbazono)ethyl]-5,7,8,9,10,12-hexahydro-naphthacene, 4-methoxy-5,12-dioxo-6,9,11-trihydroxy-7-(2,3,6-O-tridesoxy-3-amino-1-L-lyxohexosyl)-9-[1-(benzoylhydrazono)ethyl]-5,7,8,9,10,12-hexahydro-naphthacene, and 4-methoxy-5,12-dioxo-6,9,11-trihydroxy-7-(2,3,6-O-tridesoxy-3-amino-1-L-lyxohexosyl)-9-(1-formylhydrazonoethyl)-5,7,8,9,10,12-hexahydro-naphthacene.

The naphthacene derivatives of formula I may be employed as such or in the form of non-toxic salts, i.e. salts containing ions which are relatively innocuous to the animal organism in therapeutic doses of the salts, such as hydrochlorides, sulphates, nitrates, phosphates, acetates, propionates, succinates, benzoates, fumarates, maleates, tartrates, theophylline-acetates, salicylates, phenolphthalinates or methylene-bis-β-hydroxynaphthoates, metal salts such as the sodium salts, or salts with nitrogencontaining bases. They may also be employed in the form of non-toxic quaternary ammonium salts obtained by reaction of the naphthacene derivatives with organic halides, e.g. methyl, ethyl, allyl or benzyl chloride, bromide or iodide, or other reactive esters, e.g. methyl- or ethyl-sulphates, benzene sulphonates or toluene-p-sulphonates.

The following Examples, in which the percentage yields obtained are related to the theoretical yield, illustrate the invention.

EXAMPLE 1

Daunorubicin hydrochloride (0.5 g.) is dissolved in a mixture of dimethylformamide (20 cc.) and water (10 cc.). Sodium 2-aminocarbamoyl-ethanesulphonate (0.42 g.) is added. The mixture is stirred for 24 hours at ambient temperature, evaporated to dryness under reduced pressure (25 mm.Hg), and the resulting residue taken up in water (100 cc.).

A slight amount of insoluble matter is filtered off and the filtrate then lyophilised. The sodium salt of 4-methoxy-5- (or 12-) oxo-6,9,11-trihydroxy-7-(2,3,6-O-tridesoxy-3-amino-1-L-lyxohexosyl)-9-[1-(3-sulphopropionylhydrazono)ethyl]-12- (or 5-) (3-sulpho-propionylhydrazono)-5,7,8,9,10,12-hexahydronaphthacene (0.875 g.) is thus obtained in a yield of 95%.

S %: 7.47 (theory: 7.36). N % 7.7 (theory: 8.03).
Ultra-violet spectrum:
$\lambda$ max=233 nm; $\epsilon$=29,200
$\lambda$ max=252 nm; $\epsilon$=20,920
$\lambda$ max=288 nm; $\epsilon$=6,100

EXAMPLE 2

Daunorubicin hydrochloride (0.6 g.) is dissolved in ethanol (65 cc.) containing 2.5% of acetic acid, and Girard reagent T (0.369 g.) is added. The mixture is heated for 4 hours at 40° C. with stirring, evaporated to dryness under reduced pressure (25 mm.Hg), and the resulting residue taken up in water (50 cc.).

A slight amount of insoluble matter is filtered off and the filtrate is lyophilised. 4-Methoxy-5- (or 12-) oxo-6,9,11-trihydroxy-7-(2,3,6-O-tridesoxy-3-amino-1-L-lyxohexosyl)-9-[1-(trimethylammonioacetylhydrazono)ethyl]-12-(or 5) (trimethylammonioacetylhydrazono)-5,7,8,9,10,12-hexahydro-naphthacene dichloride hydrochloride (0.855 g.) is thus obtained.

Cl %: 12.07 (theory: 12.32).
Ultra-violet spectrum:
$\lambda$ max=233 nm; $\epsilon$=38,200
$\lambda$ max=252 nm; $\epsilon$=27,500
$\lambda$ max=290 nm; $\epsilon$=7,720

EXAMPLE 3

Daunorubicin hydrochloride (0.5 g.) is dissolved in ethanol (80 cc.) containing 2.5% of acetic acid. Thiosemicarbazide (0.084 g.) is added and the mixture heated for 4 hours at 40° C. with stirring. It is then stirred for 72 hours at ambient temperature, evaporated to dryness under reduced pressure (25 mm.Hg) and the dry residue taken up in water (80 cc.).

A slight amount of insoluble matter is filtered off and the filtrate then lyophilised to give 4-methoxy-5,12-dioxo-6,9,11-trihydroxy-7-(2,3,6-O-tridesoxy-3-amino-1-L-lyxohexosyl)-9-[1-(thiosemicarbazono)ethyl]-5,7,8,9,10,12-hexahydro-naphthacene hydrochloride (0.483 g.)

N %: 8.85 (theory: 8.79) S %: 5.0 (theory: 5.03).
Ultra-violet spectrum:
$\lambda$ max=232 nm; $\epsilon$=32,250
$\lambda$ max=257 nm; $\epsilon$=32,225.

EXAMPLE 4

Daunorubicin hydrochloride (0.6 g.) is dissolved in ethanol (30 cc.) containing 2.5% of acetic acid. A solution of aminoguanidine (0.151 g.) in N hydrochloric acid (1.09 cc.) is prepared separately. The two solutions are mixed and heated at 50° C. for 4 hours; the mixture is then left for 72 hours at ambient temperature and thereafter evaporated to dryness under reduced pressure (25 mm.Hg). The residue is taken up in water (60 cc.), a slight amount of insoluble matter is filtered off and the filtrate is lyophilised. 4-Methoxy-5,12-dioxo-6,9,11-trihydroxy-7-(2,3,6-O-tridesoxy-3-amino-1-L-lyxohexosyl)-9-[1-(amidinohydrazono)ethyl]-5,7,8,9,10,12-hexahydro-naphthacene dihydrochloride (0.64 g.) is thus obtained.

N %: 10.73 (theory: 10.66).
Ultra-violet spectrum:
$\lambda$ max=233 nm; $\epsilon$=45,500
$\lambda$ max=253 nm; $\epsilon$=27,820
$\lambda$ max=291 nm; $\epsilon$=8,515

EXAMPLE 5

Daunorubicin hydrochloride (0.4 g.) is dissolved in ethanol (60 cc.) containing 2.5% of acetic acid, and thiosemicarbazide (0.135 g.) is then added. The resulting mixture is heated for 12 hours to 45° C. with stirring, then evaporated to dryness under reduced pressure, and the residue is taken up in water (50 cc.). The resulting solution is lyophilised to give 4-methoxy-5- (or 12-) oxo-6,9,11-trihydroxy-7-(2,3,6-O-tridesoxy-3-amino-1-L-lyxohexosyl)-9-[1-(thiosemicarbazono)ethyl]-12- (or 5-) (thiosemicarbazono)-5,7,8,9,10,12-hexahydro-naphthacene hydrochloride (0.476 g.) in a yield of 89%.

Cl %: 4.97 (theory: 4.99) S %: 8.90 (theory: 9.02).
Ultra-violet spectrum:
$\lambda$ max=233 nm; $\epsilon$=42,000
$\lambda$ max=257 nm; $\epsilon$=31,800

EXAMPLE 6

Daunorubicin hydrochloride (10 g.) is dissolved in methanol (1500 cm$^3$) and benzene (150 cm$^3$) and 4-methylthiosemicarbazide (2.05 g.) added. The reaction medium is concentrated by distilling off 200 cm$^3$ of solvent, and heated with shaking at 60° C. for 24 hours; it is then evaporated to dryness under reduced pressure (25 mm of mercury) at 45° C. The residue is extracted by shaking vigorously with diethyl ether (2000 cm$^3$). The resulting precipitate is filtered off, washed with a 1:3 mixture (by volume) of methanol/ether and dried under reduced pressure (0.3 mm.Hg) at 20° C. The precipitate is taken up with distilled water and lyophilised. 4-methoxy-5,12-dioxo-6,9,11-trihydroxy-7-(2,3,6-O-tridesoxy-3-amino-1-L-lyxohexosyl)-9-[1-(4-methylthiosemicarbazono)ethyl]-5,7,8,9,10,12-hexahydronaphthacene hydrochloride (10.8 g.) is obtained.

N %=8.45 (theory=8.60). S %=4.89 (theory=4.92).

The 4-methylthiosemicarbazide is prepared by the method of G. PULVERMACHER, Ber., 27, 613 (1894).

EXAMPLE 7

Daunorubicin hydrochloride (9.024 g.) is dissolved in ethanol (800 cm$^3$) containing 2.5% acetic acid and benzoylhydrazide (2.162 g.) added. The mixture is heated for 24 hours at 60° C. and the resulting precipitate is filtered off, washed with ethanol (100 cm$^3$), and dried under reduced pressure (0.3 mm.Hg) at 20° C. The precipitate is taken up with distilled water, filtered to remove a slight precipitate, and lyophilised. 4-Methoxy-5,12-dioxo-6,9,11-trihydroxy-7-(2,3,6-O-tridesoxy-3-amino-1-L-lyxohexosyl)-9-[1-benzoylhydrazono-ethyl]-5,7,8,9,10,12-hexahydro-naphthacene hydrochloride (10.17 g.) is obtained.

N %=5.87 (theory=6.16).

The benzoylhydrazide is prepared by the method of B. Rogers et al., U.S. Atomic Energy Comm. L.A. 1639 (1953) [C.A. 49, 7559 i (1955)].

EXAMPLE 8

Daunorubicin hydrochloride (20 g.) is dissolved in a mixture of ethanol and acetic acid (97.5:2.5 by volume, 1500 cm$^3$) and formylhydrazine (2.4 g.) is added at 50° C. The reaction mixture is heated with agitation for 15 hours at 65° C., and then cooled for one hour in an ice-water bath to complete the precipitation observed during the heating. The mixture is filtered through sintered glass and the solid is washed with ethanol and then dried under reduced pressure (0.3 mm.Hg.) first at 20° C. and then at 45° C. 4-Methoxy-5,12-dioxo-6,9,11-trihydroxy-7-(2,3,6-O-tridesoxy-3-amino-1-L-lyxohexosyl)-9-(1-formylhydrazono-ethyl)-5,7,8,9,10,12-hexahydro-naphthacene hydrochloride (17.2 g.) is thus obtained as a red powder.

C %=54.9 (theory=55.49); H %=5.1 (theory=5.32); N %=6.7 (theory=6.93); Cl %=5.9 (theory=5.84).

The present invention includes within its scope pharmaceutical compositions which comprise at least one of the naphthacene derivatives of general formula I, or a nontoxic salt thereof, in association with a pharmaceutically-acceptable carrier or coating. In clinical practice the compounds of the present invention will normally be administered orally, parenterally or rectally.

Solid compositions for oral administration include compressed tablets, pills, powders, and granules. In such solid compositions one or more of the active compounds is, or are, admixed with at least one inert diluent such as starch, sucrose or lactose. The compositions may also comprise, as is normal practice, additional substances other than inert diluents, e.g. lubricating agents, such as magnesium stearate. Liquid compositions for oral administration include pharmaceutically-acceptable emulsions, solutions, suspensions, syrups and elixirs containing inert diluents commonly used in the art, such as water and liquid paraffin. Besides inert diluents such compositions may also comprise adjuvants, such as wetting and suspending agents, and sweetening, flavouring, perfuming and preserving agents. The compositions according to the invention, for oral administration, also include capsules of absorbable material such as gelatin containing one or more of the active substances with or without addition of diluents or excipients.

Preparations according to the invention for parenteral administration include sterile aqueous or non-aqueous solutions, suspensions, or emulsions. Examples of non-aqueous solvents or suspending media are propylene glycol, polyethylene glycol, vegetable oils such as olive oil, and injectable organic esters such as ethyl oleate. These compositions may also contain adjuvants such as preserving, wetting, emulsifying and dispersing agents. They may be sterilised by, for example, filtration through a bacteria-retaining filter, by incorporation in the compositions of sterilising agents, by irradiation or by heating. They may also be manufactured in the form of sterile solid compositions, which can be dissolved or dispersed in sterile water or some other sterile injectable medium immediately before use.

Compositions for rectal administration are suppositories which contain, in addition to the active substance, excipients such as cacao butter, a suitable wax base or solidified glycerin.

The percentage to active ingredient in the compositions of the invention may be varied, it being necessary that it should constitute a proportion such that a suitable dosage shall be obtained. The dosage will depend upon the therapeutic effect sought, the route of administration, the length of treatment, and the species of animal. In human therapy, for example in the treatment of the lymphoblastic and myeloblastic forms of acute leukaemia, and chronic myeloid leukaemia, the compositions should generally be administered so as to give, in the case of parenteral administration, doses between 2 and 10 mg./kg. of naphthacene derivative per day for an adult.

The following Example illustrates pharmaceutical compositions according to the invention.

EXAMPLE 9

A solution of the following composition is prepared:
4-methoxy-5- (or 12-) oxo-6,9,11-trihydroxy-7-(2,3,6-O- tridesoxy-3-amino-1-L-lyxohexosyl)-9-[1-(thiosemicarbazono)ethyl]-12- (or 5-) (thiosemicarbazono)-5,7,8,9,10,12-hexahydronaphthacene hydrochloride, 2.1 g.; distilled water, 100 cm³. This solution is sterilised by filtering through a bacteriostatic filter and is then divided between ampoules in a quantity of 10 cm³ per ampoule. The ampoules are thereafter lyophilised under a nitrogen atmosphere and sealed.

For parenteral administration as a medicine, an injectable solution is prepared immediately before use by adding 5 cc. of physiological serum to the contents of the ampoule. A 5 cc. solution containing 200 mg. of active product is thus obtained.

I claim:

1. A pharmaceutical composition for parenteral administration and useful for the treatment of acute myeloblastic leukaemia which comprises, as active ingredient, a naphthacene of the formula:

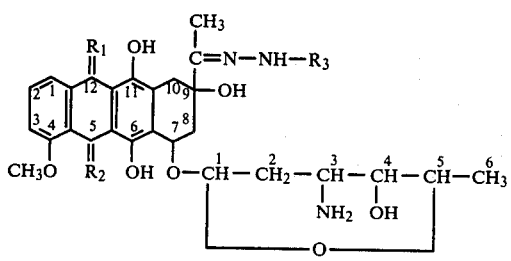

wherein one of $R_1$ and $R_2$ is oxygen and the other is oxygen or $=N-NHR_3$, and $R_3$ is alkanoyl of up to 4 carbon atoms, alkanoyl of up to 4 carbon atoms substituted by a sulphonic acid group, alkanoyl of up to 4 carbon atoms substituted by a quaternary ammonium group, thiocarbamoyl, methylthiocarbamoyl, amidino, or benzoyl, or a non-toxic salt thereof, in association with a significant amount of a sterile injectable pharmaceutically-acceptable carrier.

2. A composition according to claim 1 in which the said active ingredient is a naphthacene of the formula:

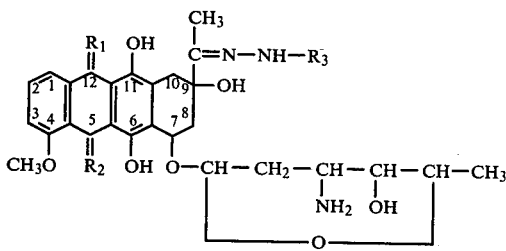

wherein one of $R_1$ and $R_2$ is oxygen and the other is oxygen or $=N-NHR_3$, and $R_3$ is alkanoyl of up to 4 carbon atoms, alkanoyl of up to 4 carbon atoms substituted by a sulphonic acid group, alkanoyl of up to 4 carbon atoms substituted by a quaternary ammonium group, thiocarbamoyl, amidino, or benzoyl, or a non-toxic salt thereof.

3. A composition according to claim 1 in which the active ingredient is 4-methoxy-5- (or 12-) oxo-6,9,11-trihydroxy-7-(2,3,6-O-tridesoxy-3-amino-1-L-lyxohexosyl)-9-[1-(3-sulphopropionylhydrazono)ethyl]-12- (or 5-) (3-sulpho-propionylhydrazono)-5,7,8,9,10,12-hexahydro-naphthacene, or a non-toxic acid addition or non-toxic metal salt thereof.

4. A composition according to claim 1 in which the active ingredient is 4-methoxy-5- (or 12-) oxo-6,9,11-trihydroxy-7-(2,3,6-O-tridesoxy-3-amino-1-L-lyxohexosyl)-9-[1-(trimethylammonioacetylhydrazono)ethyl]-12- (or 5-) (trimethylammonioacetylhydrazono)-5,7,8,9,10,12-hexahydronaphthacene dichloride, or a non-toxic acid addition salt thereof.

5. A composition according to claim 1 in which the active ingredient is 4-methoxy-5,12-dioxo-6,9,11-trihydroxy-7-(2,3,6-O-tridesoxy-3-amino-1-L-lyxohexosyl)-9-[1-(thiosemicarbazono)ethyl]-5,7,8,9,10,12-hexahydronaphthacene, or a non-toxic acid addition salt thereof.

6. A composition according to claim 1 in which the active ingredient is 4-methoxy-5,12-dioxo-6,9,11-trihydroxy-7-(2,3,6-O-tridesoxy-3-amino-1-L-lyxohexosyl)-9-[1-(amidinohydrazono)ethyl]-5,7,8,9,10,12-hexahydronaphthacene, or a non-toxic acid addition salt thereof.

7. A composition according to claim 1 in which the active ingredient is 4methoxy-5- (or 12-) oxo-6,9,11-trihydroxy-7-(2,3,6-O-tridesoxy-3-amino-1-L-lyxohexosyl)-9-[1-(thiosemicarbazono)ethyl]-12- (or 5-) (thiosemicarbazono)-5,7,8,9,10,12-hexahydro-naphthacene, or a non-toxic acid addition salt thereof.

8. A composition according to claim 1 in which the active ingredient is 4-methoxy-5,12-dioxo-6,9,11-trihydroxy-7-(2,3,6-O-tridesoxy-3-amino-1-L-lyxohexosyl)-9-[1-(4-methylthiosemicarbazono)ethyl]-5,7,8,9,10,12-hexahydro-naphthacene, or a non-toxic acid addition salt thereof.

9. A composition according to claim 1 in which the active ingredient is 4-methoxy-5,12-dioxo-6,9,11-trihydroxy-7-(2,3,6-O-tridesoxy-3-amino-1-L-lyxohexosyl)-9-[1-(benzoylhydrazono)ethyl]-5,7,8,9,10,12-hexahydro-naphthacene or a non-toxic acid addition salt thereof.

10. A composition according to claim 1 in which the active ingredient is 4-methoxy-5,12-dioxo-6,9,11-trihydroxy-7-(2,3,6-O-tridesoxy-3-amino-1-L-lyxohexosyl)-9-(1-formylhydrazonoethyl)-5,7,8,9,10,12-hexahydronaphthacene, or a non-toxic acid addition salt thereof.

11. Method for the treatment of, acute myeloblastic leukaemia in a human patient which comprises administering parenterally to the patient a quantity of from 2 to 10 mg/kg per day of a naphthacene of the formula:

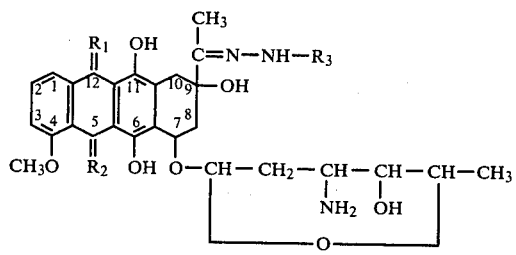

wherein one of $R_1$ and $R_2$ is oxygen and the other is oxygen or $=N-NHR_3$, and $R_3$ is alkanoyl of up to 4 carbon atoms, alkanoyl of up to 4 carbon atoms substituted by a sulphonic acid group, alkanoyl of up to 4 carbon atoms substituted by a quaternary ammonium group, thiocarbamoyl, methylthiocarbamoyl, amidino, or benzoyl, or a non-toxic salt thereof.

12. Method for the treatment of, acute myeloblastic leukaemia in a human patient which comprises administering parenterally to the patient a quantity of from 2 to 10 mg/kg per day of a naphthacene of the formula:

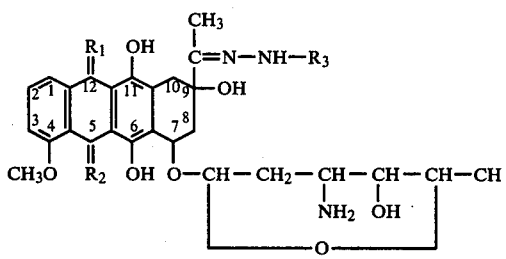

wherein one of $R_1$ and $R_2$ is oxygen and the other is oxygen or $=N-NHR_3$, and $R_3$ is alkanoyl of up to 4 carbon atoms, alkanoyl of up to 4 carbon atoms substituted by a sulphonic acid group, alkanoyl of up to 4 carbon atoms substituted by a quaternary ammonium group, thiocarbamoyl, amidino, or benzoyl, or a non-toxic salt thereof.

13. Method for the treatment of, acute myeloblastic leukaemia in a human patient which comprises administering parenterally to the patient a quantity of from 2 to 10 mg/kg per day of 4-methoxy-5- (or 12-) oxo-6,9,11-trihydroxy-7-(2,3,6-O-tridesoxy-3-amino-1-L-lyxohexosyl)-9-[1-(3-sulphopropionylhydrazono)ethyl]-12- (or 5-) (3-sulpho-propionyl-hydrazono)-5,7,8,9,10,12-hexahydronaphthacene, or a non-toxic acid addition or non-toxic metal salt thereof.

14. Method for the treatment of, acute myeloblastic leukaemia in a human patient which comprises administering parenterally to the patient a quantity of from 2 to 10 mg/kg per day of 4-methoxy-5- (or 12-) oxo-6,9,11-trihydroxy-7-(2,3,6-O-tridesoxy-3-amino-1-L-lyxohexosyl)-9-[1-(trimethylammonioacetylhydrazono)]-12- (or 5-) (trimethylammonioacetylhydrazono)-5,7,8,9,10,12-hexa-hydronaphthacene dichloride, or a non-toxic acid addition salt thereof.

15. Method for the treatment of, acute myeloblastic leukaemia in a human patient which comprises administering parenterally to the patient a quantity of from 2 to 10 mg/kg per day of 4-methoxy-5,12-dioxo-6,9,11-trihydroxy-7-(2,3,6-O-tridesoxy-3-amino-1-L-lyxohexosyl)-9-[1-(thiosemicarbazono)ethyl]-5,7,8,9,10,12-hexahydronaphthacene, or a non-toxic acid addition salt thereof.

16. Method for the treatment of, acute myeloblastic leukaemia in a human patient which comprises administering parenterally to the patient a quantity of from 2 to 10 mg/kg per day of 4-methoxy-5,12-dioxo-6,9,11-trihydroxy-7-(2,3,6-O-tridesoxy-3-amino-1-L-lyxohexosyl)-9-[1-(amidinohydrazono)ethyl]-5,7,8,9,10,12-hexahydronaphthacene, or a non-toxic acid addition salt thereof.

17. Method for the treatment of, acute myeloblastic leukaemia in a human patient which comprises administering parenterally to the patient a quantity of from 2 to 10 mg/kg per day of 4-methoxy-5- (or 12-) oxo-6,9,11-trihydroxy-7-(2,3,6-O-tridesoxy-3-amino-1-L-lyxohexosyl)-9-[1-(thiosemicarbazono)ethyl]-12- (or 5-) (thiosemicarbazono)-5,7,8,9,10,12-hexahydro-naphthacene, or a non-toxic acid addition salt thereof.

18. Method for the treatment of, acute myeloblastic leukaemia in a human patient which comprises administering parenterally to the patient a quantity of from 2 to 10 mg/kg per day of 4-methoxy-5,12-dioxo-6,9,11-trihydroxy-7-(2,3,6-O-tridesoxy-3-amino-1-L-lyxohexosyl)-9-[1-4-(methylthiosemicarbazono)ethyl]-5,7,8,9,10,12-hexahydro-naphthacene, or a non-toxic acid addition salt thereof.

19. Method for the treatment of, acute myeloblastic leukaemia in a human patient which comprises administering parenterally to the patient a quantity of from 2 to 10 mg/kg per day of 4-methoxy-5,12-dioxo-6,9,11-trihydroxy-7-(2,3,6-O-tridesoxy-3-amino-1-L-lyxohexosyl)-9-[1-(benzoylhydrazono)ethyl]-5,7,8,9,10,12-hexahydro-naphthacene or a non-toxic acid addition salt thereof.

20. Method for the treatment of, acute myeloblastic leukaemia in a human patient which comprises administering parenterally to the patient a quantity of from 2 to 10 mg/kg per day of 4-methoxy-5,12-dioxo-6,9,11-trihydroxy-7-(2,3,6-O-tridesoxy-3-amino-1-L-lyxohexosyl)-9-(1-formyl-hydrazonoethyl)-5,7,8,9,10,12-hexahydronaphthacene, or a non-toxic acid addition salt thereof.

* * * * *